(12) United States Patent
Lam

(10) Patent No.: US 7,476,215 B2
(45) Date of Patent: Jan. 13, 2009

(54) AUTOMATIC RETRACTABLE SAFETY SYRINGE

(76) Inventor: Choi Fat Lam, 8503 Vaiden Falls Ct., Houston, TX (US) 77083

( * ) Notice: Subject to any disclaimer, the term of this patent is extended or adjusted under 35 U.S.C. 154(b) by 526 days.

(21) Appl. No.: 11/232,067

(22) Filed: Sep. 21, 2005

(65) Prior Publication Data

US 2007/0066936 A1    Mar. 22, 2007

(51) Int. Cl.
*A61M 5/00* (2006.01)
*A61M 5/32* (2006.01)

(52) U.S. Cl. ...................... 604/110; 604/192
(58) Field of Classification Search .............. 604/110, 604/197
See application file for complete search history.

(56) References Cited

U.S. PATENT DOCUMENTS

| | | | |
|---|---|---|---|
| 4,790,822 A | 12/1988 | Haining | |
| 4,950,251 A | 8/1990 | Haining | |
| 5,000,736 A | 3/1991 | Kaufhold, Jr. et al. | |
| 5,152,750 A | 10/1992 | Haining | |
| 5,385,551 A | 1/1995 | Shaw | |
| 5,885,257 A | 3/1999 | Badger | |
| 6,846,301 B2 | 1/2005 | Smith et al. | |
| 2003/0187400 A1 | 10/2003 | Liao | |
| 2004/0087907 A1* | 5/2004 | Smith et al. | 604/228 |
| 2005/0096604 A1 | 5/2005 | Maggioni | |

FOREIGN PATENT DOCUMENTS

WO    WO 03/051436 A2 *   6/2003   .................. 604/240

* cited by examiner

Primary Examiner—Nicholas D Lucchesi
Assistant Examiner—Victoria P Campbell
(74) Attorney, Agent, or Firm—Richard L. Moseley

(57) ABSTRACT

A syringe includes a retractable needle assembly comprising a needle seat, a hypodermic needle, and a barrel. A hollow plunger is slidably mounted within the barrel. A seal is provided between the plunger and barrel to prevent air from passing into or out of the barrel. A piston is slidably mounted within the plunger such that movement of the plunger into the fill position locks the piston in place. A seal between the piston and the interior of the plunger prevents air or fluid from passing into the plunger. As the plunger is depressed the plunger moves in the barrel while in the piston is stationary. The relative axial movement of the plunger in relation to the piston causes a vacuum to be created within the plunger. The plunger in the fully depressed position releases the needle carrier and the vacuum pulls the needle carrier and needle into the hollow plunger.

8 Claims, 6 Drawing Sheets

AUTOMATIC RETRACTABLE SAFETY SYRINGE

BACKGROUND OF THE INVENTION

1. Field of the Invention

The present invention relates generally to disposable hypodermic syringes. More particularly the invention relates to safety syringes wherein the hypodermic needle is retractable into the barrel of the syringe after use to prevent accidental needle prick. Most particularly the invention relates to a safety syringe which is automatically retracted into the barrel after use by a vacuum created within the barrel by movement of the plunger.

2. Related Art

Due to the recent advent of the AIDS virus, which may be contracted by contaminated hypodermic syringes, there have been several retractable needle hypodermic syringes invented and patented. The retraction of the needle into the barrel of the syringe after use reduces the risk of "needle prick", or the accidental pricking of the person giving the injection after the syringe has been used.

The prior art discloses different syringes which accomplish the retraction. Some of the recently patented retractable needle syringes include U.S. Pat. No. 4,692,156 (Haller); U.S. Pat. No. 4,675,005 (DeLuccia); U.S. Pat. No. 4,747,830 (Gloyer, et al); U.S. Pat. No. 4,790,822 (Haining) and U.S. Pat. No. 4,950,251 (Haining). All of the syringes disclosed include a hypodermic needle mounted on a carrier which is slidable in the barrel. The plunger is locked to this carrier after the injection has been given and is withdrawn up into the barrel by withdrawal of the plunger. One disadvantage of the above syringes is that the locking mechanism takes up some space in the barrel of the syringe and may prevent all of the measured liquid from being ejected by the plunger. This problem is exacerbated in the very small syringes such as the 1 cc tuberculin type. The liquid left in the barrel may be a substantial portion of the measured dose. In addition the narrowness of the barrel of the 1 cc syringe makes it difficult to design a needle carrier and locking mechanism that will fit in the barrel without enlarging the diameter so much as to make the calibration useless.

Automatic retractable needle syringes have become more popular with the first syringes having springs which when released retract the needle into the barrel. One example of this type is U.S. Pat. No. 5,885,257 (Badger).

Vacuum powered retraction mechanisms are disclosed in U.S. Pat. No. 5,000,736 (Kaufhold et al) and U.S. Pat. No. 6,846,301 (Smith et al). In the first the vacuum, is provided in the syringe as shipped and breaking a seal activates the mechanism. In the second the vacuum is created by movement of the plunger within the barrel. The main drawback to the second invention is that the entire barrel has to be evacuated and the force applied over the entire cross sectional area is relatively small.

SUMMARY OF THE INVENTION

The present invention is directed to a safety syringe that retracts its needle into the syringe barrel to prevent the used from accidental needle prick. The retractable needle protects various people, including healthcare workers, their patients and sanitation workers involved with disposal of medical waste. The invention may prevent or reduce injuries ranging from minor skin lacerations to serious contamination by medications, germs or viruses. The syringe is preferably a disposable, single use device, and may be available in various sizes and shapes. A syringe according to this invention may also be used in non-medical applications, such as chemical handling processes and or in analytical applications.

A preferred embodiment includes a retractable needle assembly comprising a needle seat for supporting a hypodermic needle, and a generally tubular body which comprises the barrel and serves as a reservoir for injectable or withdrawn fluid. The barrel is open at both ends to receive a plunger at the plunger (proximal) end and a needle at the opposite (distal) end. A hollow plunger is slidably mounted within the barrel and extends from the plunger end for engagement by the user. A seal is provided between the plunger and barrel to prevent air from passing into or out of the barrel around the plunger and through the plunger end. A piston is slidably mounted within in the plunger such that movement of the plunger into the fill position locks the piston in place. A seal between the piston and the interior of the plunger prevents air or fluid from passing by the piston into the plunger. As the plunger is depressed to inject the fluid the plunger moves axially in the barrel while the piston is stationary. The relative axial movement of the plunger in relation to the piston causes a vacuum to be created within the plunger. The relatively smaller cross section of the plunger as compared to the barrel produces a corresponding greater vacuum force. The plunger in the fully depressed position releases the needle carrier from the end of the barrel and the vacuum pulls the needle carrier and needle into the hollow plunger.

DESCRIPTION OF THE PREFERRED EMBODIMENT

Figure 1:
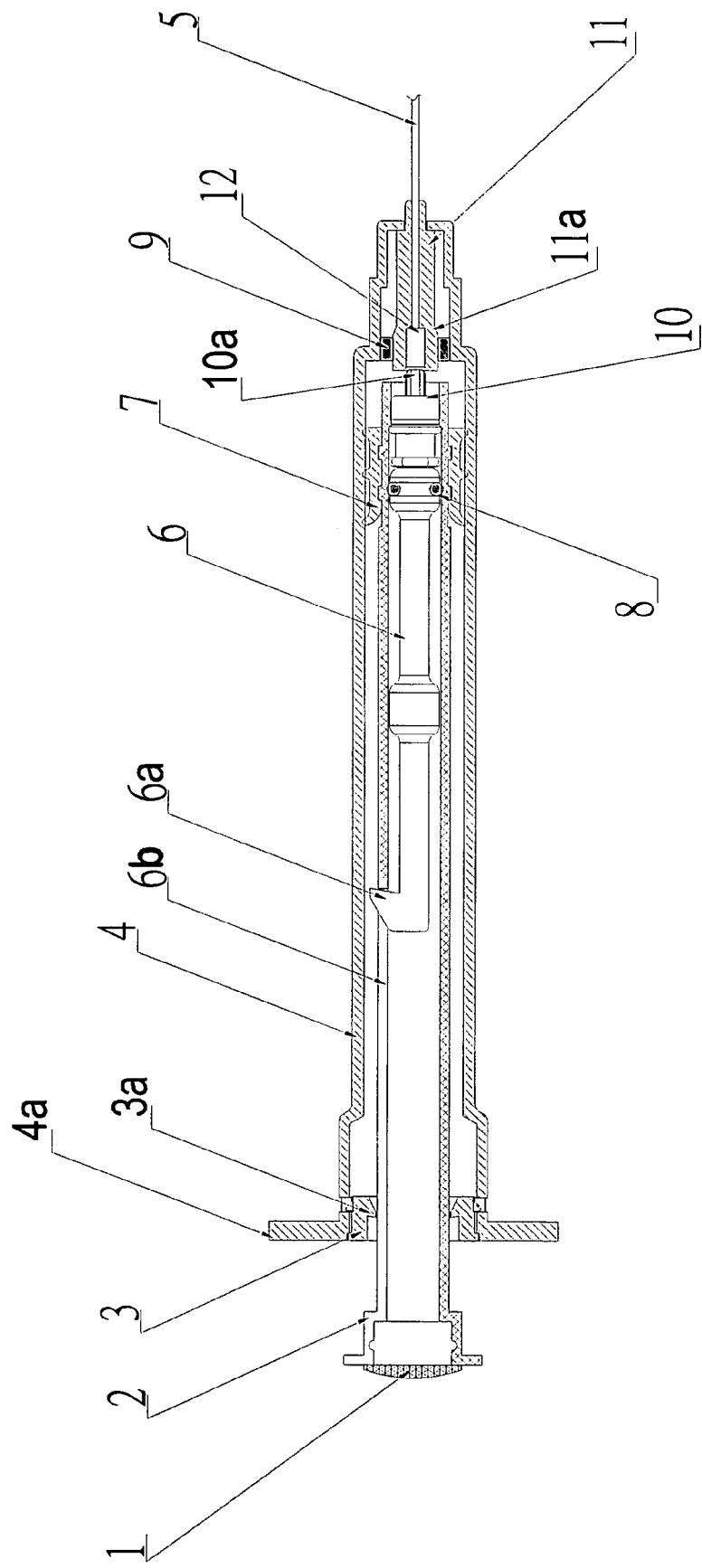
FIG. 1 is a side elevational view of the preferred embodiment of the invention as the syringe is shipped ready for use.

For a detailed description of the preferred embodiment the reader is directed to accompany FIGURES in which like components are given like reference numerals. There is shown a retractable needle syringe having a barrel 4 having finger flanges 4a at the proximal end and a hypodermic needle 5 mounted at the distal end. A hollow plunger 2 having a plunger cover 1 at the proximal end and a plunger seal 7 about the exterior of the distal end is slidably mounted within the barrel 4 with a plunger vacuum seal 10 releasably secured in the distal end. A barrel stopper 3 is secured at the proximal end of the barrel 4 to prevent air from entering the barrel at the proximal end around the plunger 2. A needle seat washer 9 surrounds the needle mounting 11 and retains the needle 5 and needle mounting 11 in the distal end of the barrel 4. A piston 6 is slidably mounted within the hollow plunger 2 having a piston vacuum seal 8 at the distal end and a piston lock 6a at the proximal end. A nipple 10a on plunger vacuum seal 10 is adapted to engage into cavity 12 in the proximal end of the needle mounting 11. The needle seat washer 9 can be moved axially along needle mounting 11 past shoulder 11a onto reduced cross sectional area to release the needle mounting 11 and needle 5 from the distal end of the barrel 4. The piston lock 6a protrudes though a longitudinal slot 6b in the wall of the hollow plunger 2 which extends from near the proximal end to the position where the lock 6a is shown to rest in FIG. 1.

Figure 2:
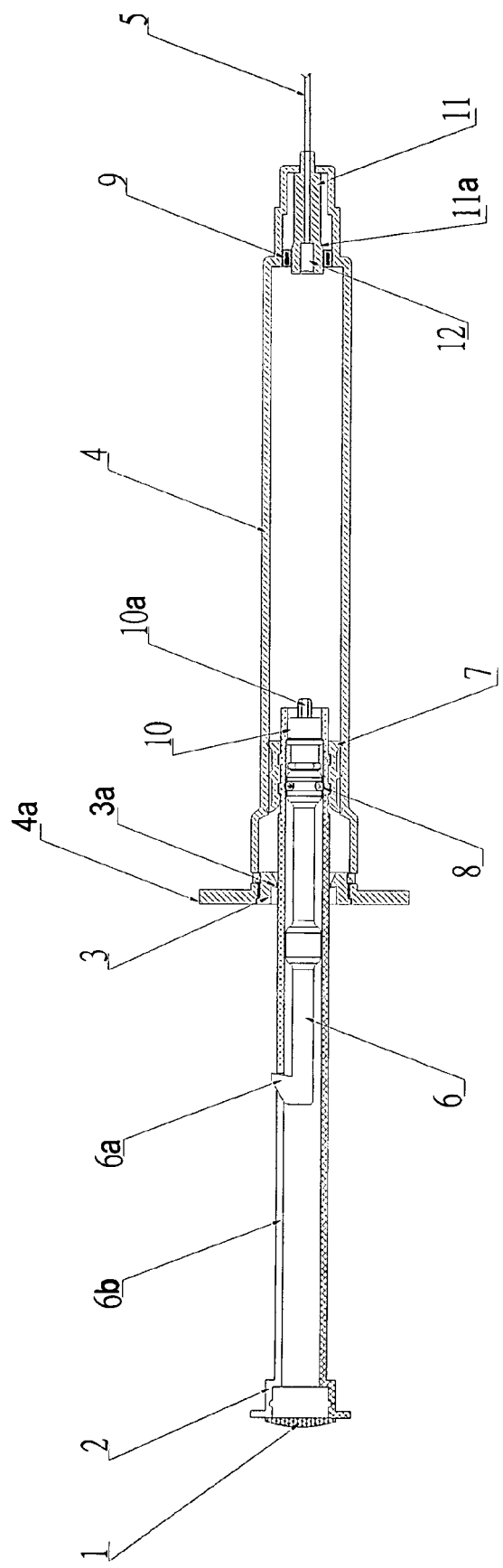
FIG. 2 is a side elevational view of the preferred embodiment of the invention with the plunger retracted in the "fill" position.
Figure 3:
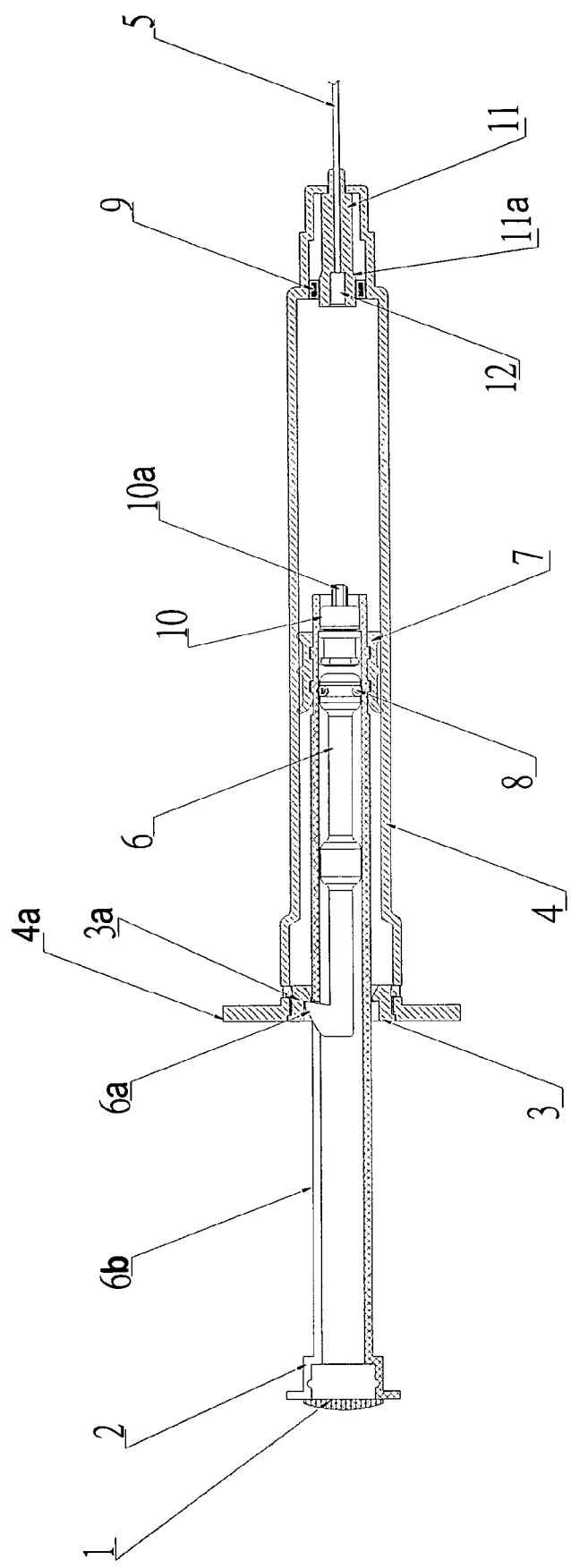
FIG. 3 is a side elevational view of the preferred embodiment of the invention with the plunger partially depressed.
Figure 4:
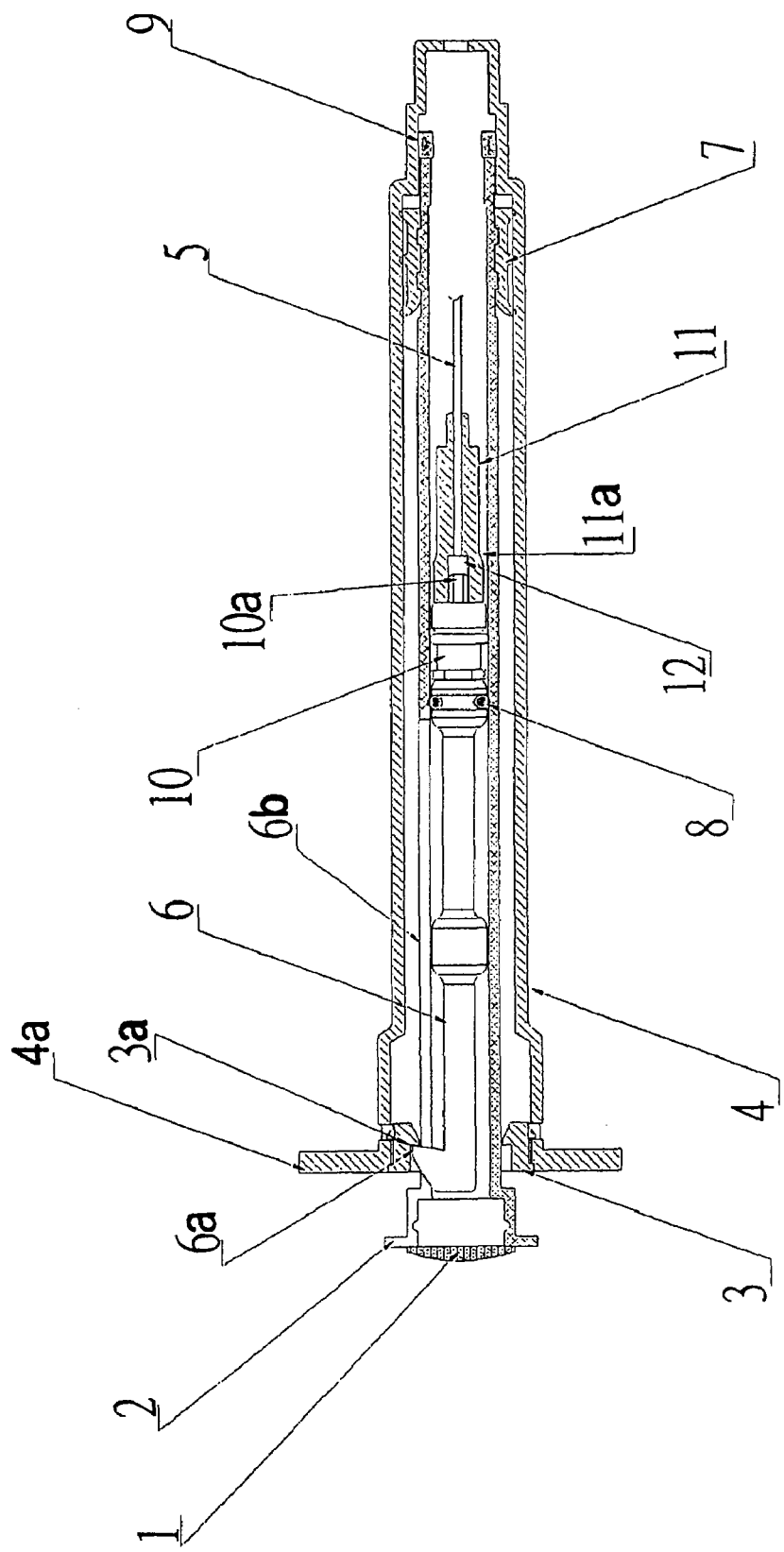
FIG. 4 is a side elevational view of the preferred embodiment of the invention with the needle retracted into the barrel.
Figure 5:
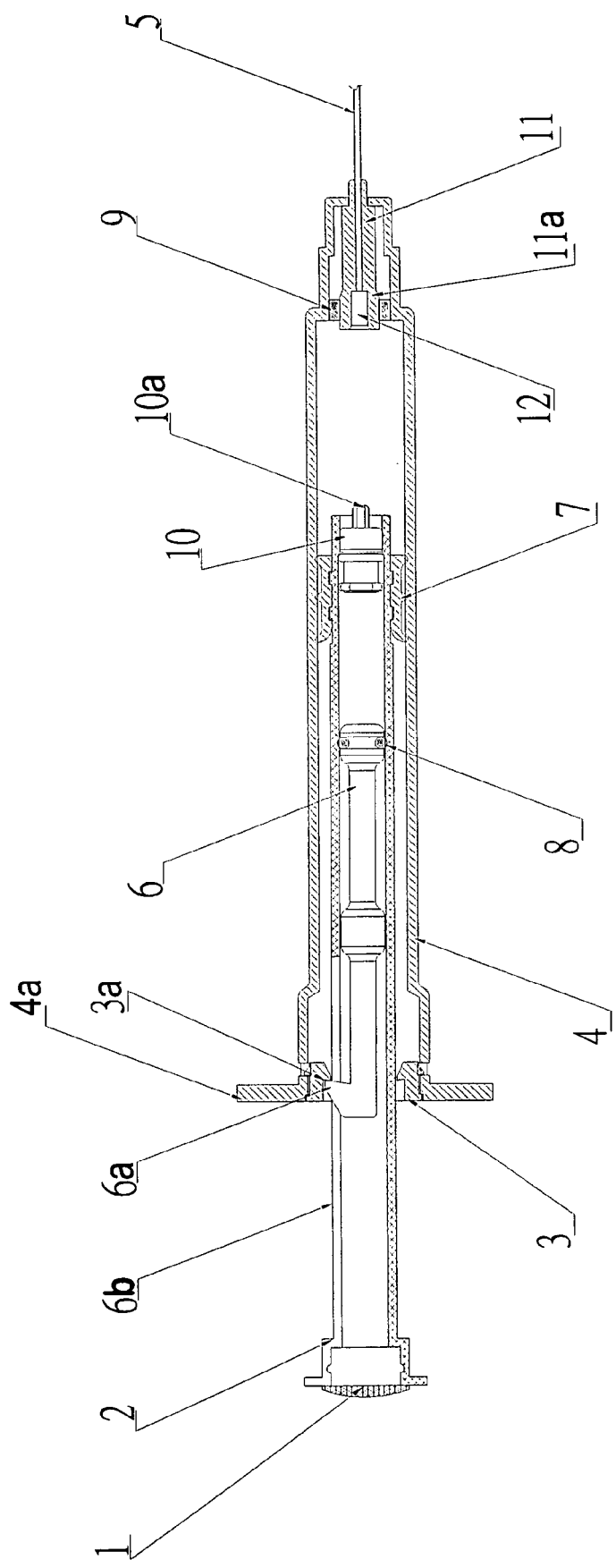
FIG. 5 is a side elevational view of the preferred embodiment of the invention with the plunger depressed further than in FIG. 3.

The syringe is shipped in the configuration shown in FIG. 1 with the piston lock 6a inside the barrel 4. When the plunger is withdrawn to fill the syringe the piston lock 6a extends radially out of the barrel 4 through slot 6b as shown in FIG. 2. As the plunger 2 is depressed the piston lock 6a engages the upper surface of the plunger stopper 3 as shown in FIG. 3. As the plunger 2 is further depressed as shown in FIG. 5 the piston 6 is retained in place by the piston lock 6a which causes relative movement between the plunger 2 and the piston 6 creating a vacuum in the space between the piston vacuum seal 8 and the plunger vacuum seal 10.

Figure 6:
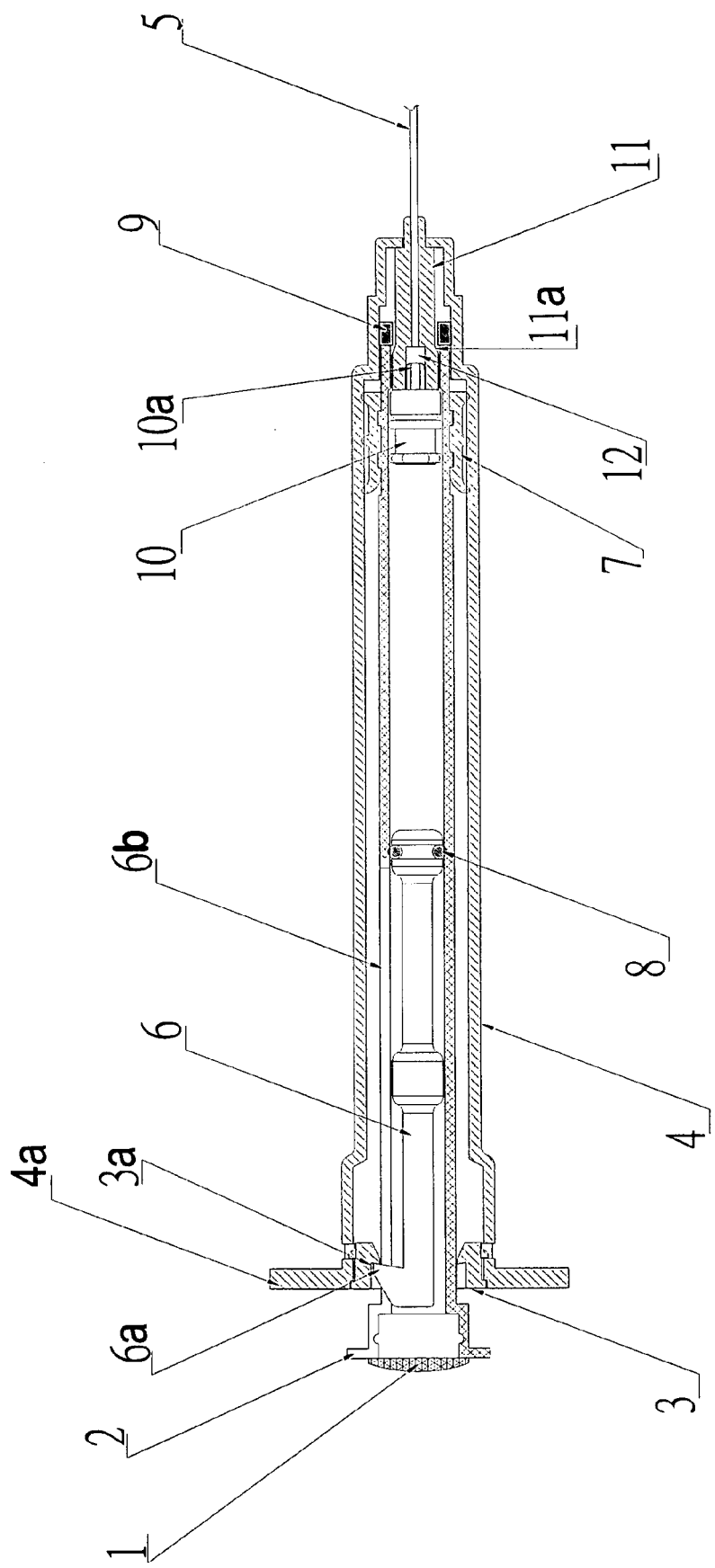
FIG. 6 is a side elevational view of the preferred embodiment of the invention with the plunger in the fully depressed position.

After use and after the needle 5 has been removed from the patient the plunger 2 is further depressed as shown in FIG. 6 the distal end of the plunger is pressed against seat washer 9 which move the seat washer 9 past the shoulder 11a and onto reduced cross sectional area and releases the needle mounting 12 and needle 5 from the distal end of the barrel 4. The nipple 10a engages the cavity 12 and further pressure moves the plunger seal 10 upward into the hollow plunger 2 releasing the vacuum and pulling the needle mounting 12 and needle 5 and plunger vacuum seal 10 upward into the hollow plunger 2 removing the needle 5 from the hazardous exposed position.

The terms proximal and distal have the following meaning:
proximal—towards the user or applier;
distal—towards the patient (or needle holding end).

As such the terms may be applied as adjectives on any part of the syringe. Every part has a proximal end and a distal end.

The foregoing description of the invention has been directed to a particular preferred embodiment of the present invention for the purposes of explanation and illustration. It will be apparent to those skilled in the art that many modifications and changes in the apparatus may be made without departing from the scope and spirit of the invention. It is therefore intended that the following claims cover all equivalent modifications and variations as fall within the scope of the invention as defined by the claims.

The invention claimed is:

1. A retractable needle syringe comprising:
    a hollow cylindrical barrel having a proximal end and a distal end;
    a hollow cylindrical plunger slidably mounted within said barrel;
    a hypodermic needle releasably secured at the distal end by a seat washer;
    a piston slidably mounted within said hollow plunger; and
    a piston lock which engages said piston at the proximal end of said barrel and holds the piston stationary in relation to the plunger and allows relative movement of the plunger around the piston as the plunger is depressed, and creates a vacuum within said hollow plunger.

2. The retractable needle syringe according to claim 1 further comprising a barrel stopper at the proximal end of said barrel.

3. The retractable needle syringe according to claim 1 further comprising a plunger seal mounted on the external surface of the distal end of said plunger.

4. The retractable needle syringe according to claim 1 further comprising a piston vacuum seal slidably mounted at the distal end of said piston.

5. The retractable needle syringe according to claim 1 further comprising a needle mount holding said hypodermic needle.

6. The retractable needle syringe according to claim 4 wherein said seat washer is snugly fit between the external surface of the proximal end of said needle mount and the internal surface of the distal end of said barrel.

7. The retractable needle syringe according to claim 6 wherein said needle mount further comprises a reduced cross sectional area toward the distal end and said seat washer is moveable by the distal end of said plunger onto said reduced cross sectional area to release said hypodermic needle and needle mount from the distal end of said barrel.

8. A retractable needle syringe comprising:
    a hollow cylindrical barrel having a proximal end and a distal end;
    a barrel stopper at the proximal end of said hollow barrel;
    a hollow cylindrical plunger slidably mounted within said barrel;
    a plunger seal mounted on the external surface of the distal end of said plunger;
    a needle mount holding a hypodermic needle which is releasably secured at the distal end by a seat washer which fits snugly between the external surface of the proximal end of said needle mount and the internal surface of the distal end of said barrel;
    said needle mount comprising a reduced cross sectional area toward the distal end;
    said seat washer being moveable to said reduced cross sectional area by the distal end of said plunger;
    a piston slidably mounted within said hollow plunger;
    a piston vacuum seal slidably mounted at the distal end of said piston; and
    a piston lock which engages said piston at the proximal end of said barrel and holds the piston stationary in relation to the plunger and allows relative movement of the plunger around the piston as the plunger is depressed, and creates a vacuum within said hollow plunger.

\* \* \* \* \*